United States Patent [19]

London et al.

[11] Patent Number: 5,225,440
[45] Date of Patent: Jul. 6, 1993

[54] ATTENUATION OF THE OPIOID WITHDRAWAL SYNDROME BY INHIBITORS OF NITRIC OXIDE SYNTHASE

[75] Inventors: Edythe D. London, Baltimore; Alane S. Kimes, Perry Hall, both of Md.

[73] Assignee: The United States of America as represented by the Department of Health and Human Services, Washington, D.C.

[21] Appl. No.: 759,999

[22] Filed: Sep. 13, 1991

[51] Int. Cl.$^5$ .................. A61K 31/24; A61K 31/195
[52] U.S. Cl. ...................................... 514/535; 514/561
[58] Field of Search ............................... 514/561, 535

[56] References Cited

PUBLICATIONS

Dwyer et al (1991) Biochemical and Biophysical Research Communications 176(3): 1136–1141.
J. H. Jaffe, Goodman and Gilman's Pharmacological Basis of Therapeutics, Ch. 22, pp. 560–561 (1991).
Fudala et al (1990) Clin. Pharmacol. Thera. 47(4):525–534.
J. Garthwaite (1991) TINS 14(2):60–67.
McCall et al (1991) Br. J. Pharmacol. 102:234–238.
Olney et al (1989) Science 244:1360–1362.
Preprint of Rasmussen et al (1991) European Journal of Pharmacology 197: 9–16.
Trujillo et al (1991) Science 251:85–87.

*Primary Examiner*—S. J. Friedman
*Attorney, Agent, or Firm*—Birch, Stewart, Kolasch & Birch

[57] ABSTRACT

A method of attenuating the symptoms of opioid withdrawal in a human or animal subject comprises administering to the subject an effective opioid withdrawal symptom attenuating amount of an inhibitor of nitric oxide synthase (NOS) for a period of time effective to attenuate such symptoms upon opioid withdrawal. NOS inhibitors useful in the present method include, for example, L-N$^G$-nitroarginine, esters of L-N$^G$-nitroarginine, L-N$^G$-monomethylarginine, L-N$^G$-benzylarginine, L-N$^G$-aminoarginine, iminoethylornithine, and pharmaceutically acceptable salts thereof. These compounds can be used alone or in combination, in conjunction with conventional drugs, such as $\alpha_2$-adrenoceptor agonists, mixed agonist-antagonist opioids, and NMDA antagonists, to attenuate the symptoms of opioid withdrawal. Effective doses of NOS inhibitors range from about 1 µg/kg/day to about 30 mg/kg/day, administered over the course of about 1 hour to about six days, followed by opioid withdrawal.

15 Claims, 3 Drawing Sheets

Nitroarginine dose response effects on withdrawal signs

*Significantly different from saline-treated control group

Nitroarginine dose response effect on weight loss due to diarrhea

*Significantly different from saline-treated control group

Lack of effect of nitroarginine on locomotor activity

Time course of the effect of nitroarginine on wet dog shakes

Significant treatment effect by 2 way ANOVA
(* 1 single injection 1 hour before NPMW)

FIG. 5

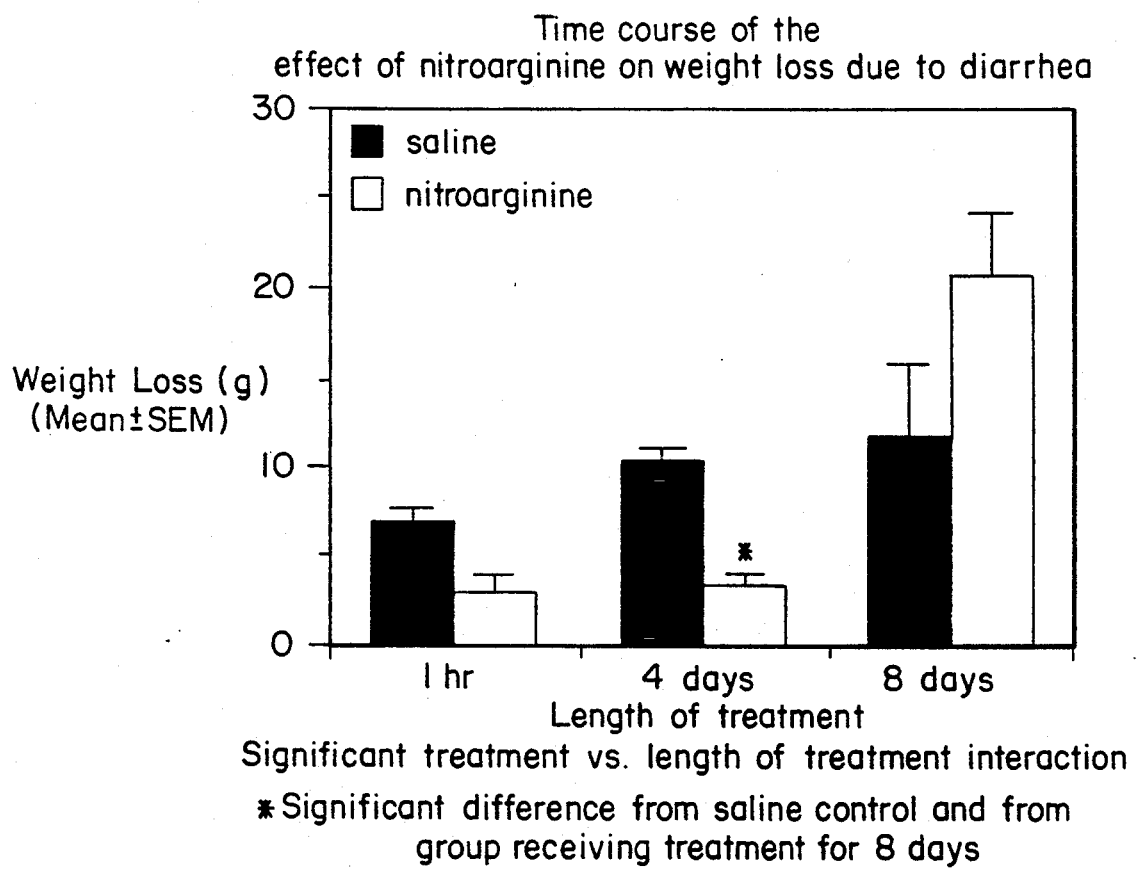

Time course of the effect of nitroarginine on weight loss due to diarrhea

Significant treatment vs. length of treatment interaction

*Significant difference from saline control and from group receiving treatment for 8 days

FIG. 6

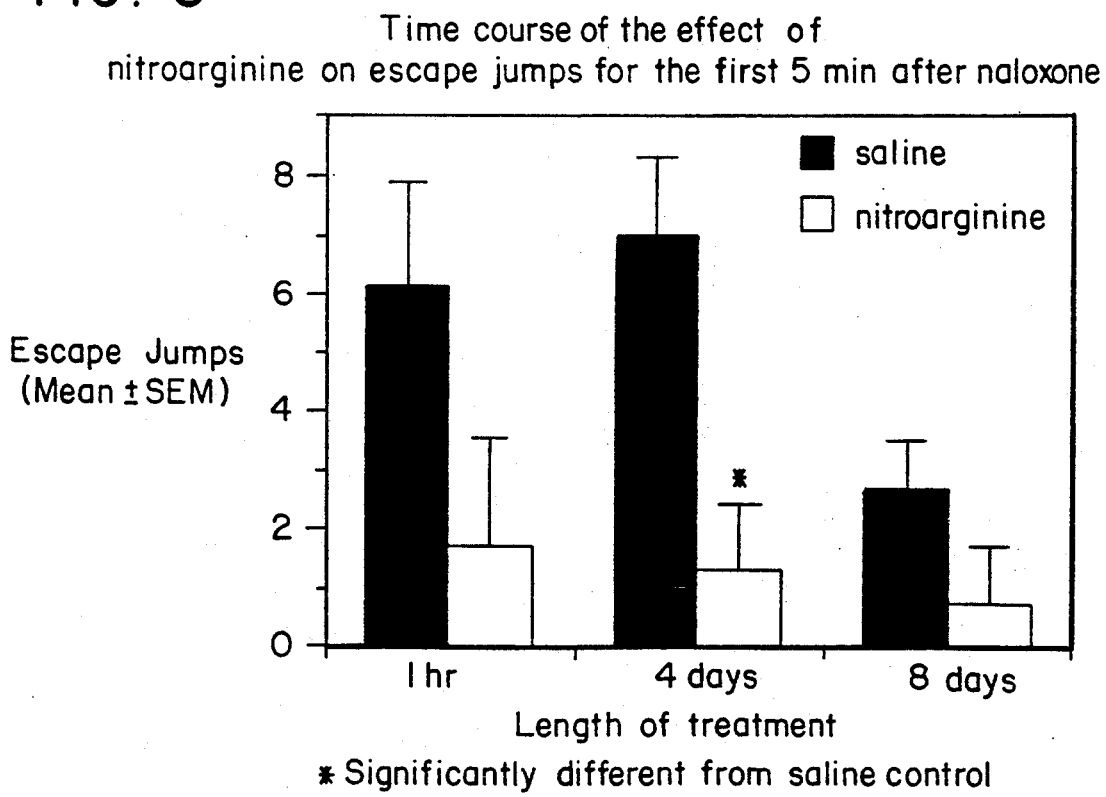

Time course of the effect of nitroarginine on escape jumps for the first 5 min after naloxone

* Significantly different from saline control

ATTENUATION OF THE OPIOID WITHDRAWAL SYNDROME BY INHIBITORS OF NITRIC OXIDE SYNTHASE

BACKGROUND OF THE INVENTION

1. Field of the Invention

The present invention relates to the use of inhibitors of nitric oxide synthase (NOS) for the attenuation of the opioid withdrawal syndrome. It is applicable to human drug addicts who are dependent on drugs like heroin, or who have been maintained for a period of time on methadone, and wish to be completely free of drugs.

2. Description of Related Art

Two major classes of drugs are presently used to attenuate the opioid withdrawal syndrome. The first class includes $\alpha_2$-adrenoceptor agonists, of which clonidine is the most commonly used (J. H. Jaffe, "Drug addiction and drug abuse," *The Pharmacological Basis of Therapeutics*, A. G. Gilman et al., eds., Pergamon Press, New York, 1991, pp. 522-573). $\alpha_2$-Adrenoceptor agonists presumably act on the same neurons, but at a different receptor, as those affected by opioids (Aghajanian, G. K., "The neurobiology of opiate withdrawal: receptors, second messengers, and ion channels," *Psychiatry Letter* III:57-60, 1985). Clonidine is an effective attenuator of the opioid withdrawal syndrome. The major problem with its use, however, is that it lowers blood pressure. Therefore, its effectiveness is limited by the susceptibility of the patient to this effect. Another drug currently being tested for the treatment of opioid withdrawal is the mixed agonist-antagonist opioid buprenorphine (Mello et al., "Buprenorphine effects on human heroin self-administration." *J. Pharmacol. Exp. Ther.*, 223:30-39, 1982). Presumably, mixed agonist-antagonists work to attenuate the withdrawal syndrome at the opioid receptor itself. This drug is also effective, but suffers from potential abuse liability because of its opioid agonist properties (Fudala et al., "Use of buprenorphine in the treatment of opioid addiction. II. Physiologic and behavioral effects of daily and alternate-day administration and abrupt withdrawal," *Clin. Pharmacol. and Ther.*, 47:525-534, 1990).

Data from animal experiments have linked opioid withdrawal and activation of glutamatergic neurotransmission (Rasmussen et al., "Withdrawal-induced activation of locus coeruleus neurons in opiate-dependent rats: attenuation by lesions of the nucleus paragigantocellularis," *Brain Research* 505:346-350, 1989; Rasmussen et al., "NMDA antagonists suppress behaviors but not norepinephrine turnover or locus coeruleus unit activity induced by opiate withdrawal," *Eur. J. Pharmacol.* 197:9-16, 1991). Recently, Trujillo et al. ("Inhibition of Morphine Tolerance and Dependence by the NMDA Receptor Antagonist MK-801," *Science* 251:85-87, 1991) reported that inhibition of N-methyl-D-aspartate (NMDA)-type glutamate receptor with MK-801 effectively attenuates jumping behavior observed in opioid-dependent rats during withdrawal, suggesting a new intervention strategy, i.e., inhibition of the NMDA neurotransmission. The class of drugs to which MK-801 belongs blocks the NMDA-gated ionic channel. Drugs of this class, which includes phencyclidine, have abuse liability, and produce untoward side effects such as hallucinations and bizarre behavior. Moreover, they produce neurotoxicity, which limits their use as pharmaceuticals (Olney et al., "Pathological changes induced in cerebrocortical neurons by phencyclidine and related drugs," *Science* 244:1360-1362, 1989).

SUMMARY OF THE INVENTION

New information concerning NMDA-type glutamatergic neurotransmission indicates that some of the consequences of activation of this receptor are mediated through nitric oxide, which acts as an intercellular messenger (Garthwaite, J., *Trends in Neuroscience* 14:60-67, 1991). Inhibition of the synthetic enzyme for nitric oxide, nitric oxide synthase (NOS), through compounds such as $N^G$-nitroarginine (nitroarginine) has profound inhibitory effects on several consequences of NMDA receptor activation. For example. $N^G$-nitroarginine blocks neurotoxicity and stimulation of cyclic GMP production in cultured neurons (Dawson et al., "Nitric oxide mediates glutamate neurotoxicity in primary cortical cultures," *Proc. Natl. Acad. Sci. USA* 88: 6368-6371, 1991). Thus, inhibition of nitric oxide synthase appears to provide a means to antagonize the effects of NMDA receptor activation while bypassing an action on the NMDA-gated ion channel (i.e., dizocilpine-like action). Accordingly, this lead the present inventors to test the effects of inhibition of NOS with nitroarginine on opioid withdrawal.

The approach to attenuation of the opioid withdrawal syndrome encompassed by the present invention is radically different from any approach in current clinical use. The site of intervention is not the opioid receptor (buprenorphine), or even a receptor which is colocalized with the opioid receptor (clonidine).

The present approach also differs substantially from that cited in previous reports on interference with the NMDA receptor. By interfering with NMDA-type glutamatergic neurotransmission at a part of the pathway that is remote from the receptor, the potential for abuse liability should be substantially reduced, as should the untoward psychiatric manifestations and toxicity of drugs like MK-801.

The present novel approach possesses the following advantages:

(a) Animals receiving nitroarginine do not exhibit lower blood pressure. In fact, treatment with nitroarginine produces moderate elevations in blood pressure.

(b) Data, infra, disclose that nitroarginine effectively reduces several signs of opioid withdrawal (wet dog shakes, diarrhea, abnormal posturing) without affecting locomotor activity (FIG. 3). Clonidine produces similar attenuation of wet dog shakes, diarrhea and abnormal posturing, but increases other withdrawal signs substantially (locomotor activity and jumping).

Accordingly, it is an object of the present invention to provide a method for attenuating the symptoms of opioid withdrawal in a human or animal subject, comprising administering to said subject an effective opioid withdrawal symptom attenuating amount of a nitric oxide synthase inhibitor for a period of time effective to attenuate said symptoms upon opioid withdrawal.

Further scope of the applicability of the present invention will become apparent from the detailed description and drawings provided below. However, it should be understood that the detailed description and specific examples, although indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which:

FIG. 5 shows the time course of the effect of nitroarginine on weight loss due to diarrhea in rats;

FIG. 6 shows the time course of the effect of nitroarginine on escape jumps for the first five minutes after naloxone administration in rats.

DETAILED DESCRIPTION OF THE INVENTION

The entire contents of each of the references cited in the present specification are herein incorporated by reference in their entirety.

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

Dose Response Effects

Figure 1:
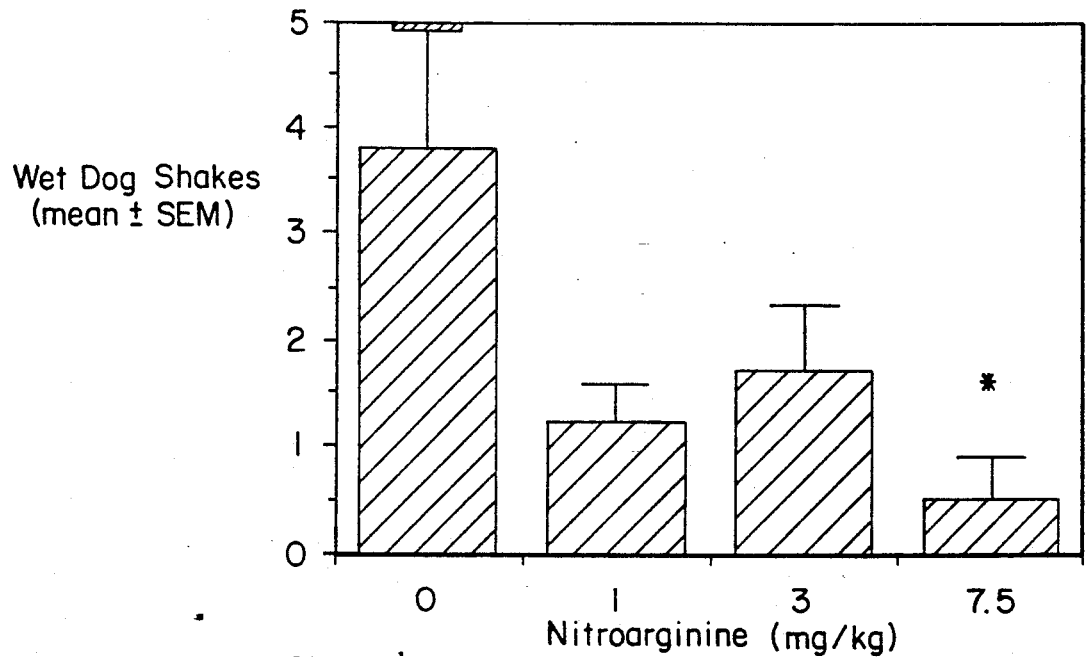
FIG. 1 shows nitroarginine dose response effects on withdrawal signs in rats.
Figure 2:
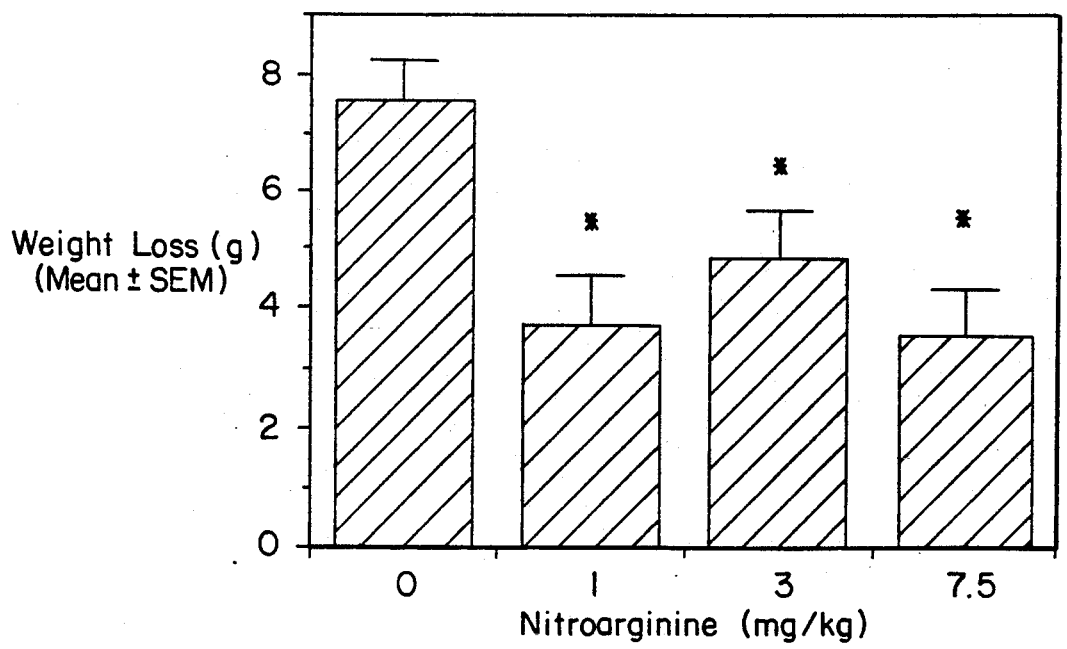
FIG. 2 shows nitroarginine dose response effects on weight loss due to diarrhea in rats.
Figure 3:
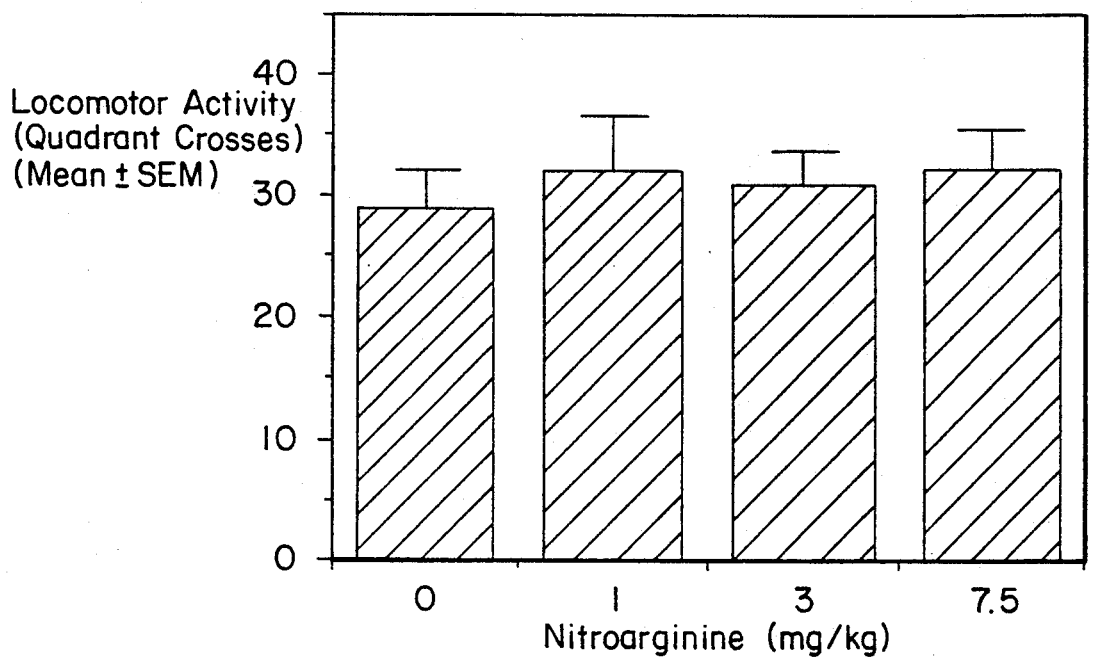
FIG. 3 shows the lack of effect of nitroarginine on locomotor activity in rats.

Morphine pellets were implanted under halothane anesthesia in four month old Fisher-344 rats on a schedule that has been previously shown to produce morphine dependence (Kimes et al., "Glucose utilization in the rat brain during chronic morphine treatment and naloxone-precipitated morphine withdrawal," *J. Pharmacol. Exp. Ther* 248:538–545, 1989). Rats received one pellet (University of North Carolina School of Pharmacy, Drug Products Program, Chapel Hill, N.C.) containing 75 mg morphine on the first treatment day, and two pellets 3 days later. As nitroarginine has been shown to inhibit cerebral NOS maximally after 4 days of treatment (Dwyer et al., "Nitric oxide synthase: irreversible by L-N$^G$-nitroarginine," *Biochemical and Biophysical Research Communications* 176 1136–1141, 1991), it was administered for 4 days in the first experiment. Rats were given nitroarginine by intraperitoneal injection twice a day for 4 days, starting on the day the second set of morphine pellets were implanted. Opioid withdrawal was initiated on the 8th day by an injection of 0.5 mg/kg naloxone. The rats were placed in a plexiglas ® observation chamber, and their behavior was observed for 15 min. Opioid withdrawal signs in animals receiving one of three doses of nitroarginine (1 mg/kg, 3 mg/kg and 7.5 mg/kg) were compared to opioid withdrawal signs in animals receiving no nitroarginine. Nitroarginine reduced several signs of opioid withdrawal, such as wet dog shakes and weight loss, in a dose-responsive fashion (FIG. 1 and FIG. 2). As shown in FIG. 3, nitroarginine had no effect on locomotor activity.

Time Course Data

Figure 4:
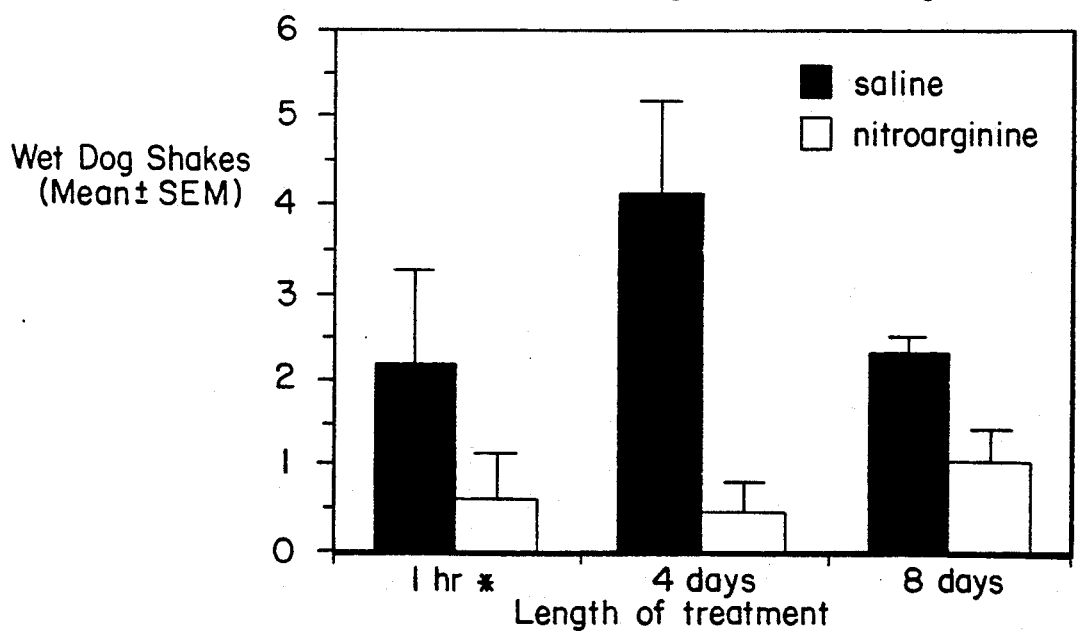
FIG. 4 shows the time course of the effect of nitroarginine on wet dog shakes in rats.

To establish the most effective timing of administration of nitroarginine on opioid withdrawal, nitroarginine (7.5 mg/kg) was administered via two additional treatment regimens: by continuous infusion via Alzet ® pumps starting at the time of the first morphine pellet implantation, and by a single injection 1 hour before opioid withdrawal was precipitated by the opioid antagonist, naloxone. The data show that nitroarginine is effective in reducing some of the opioid withdrawal symptoms irrespective of the administration schedule (FIG. 4). However, the greatest number of symptoms affected and the magnitude of the effect was usually greatest when the drug was administered for 4 days before the precipitated withdrawal (FIG. 5 and FIG. 6).

Significance of the Experimental Results

As disclosed by the data discussed supra, inhibition of the production of nitric oxide by inhibiting its synthetic enzyme reduces the severity of the opioid withdrawal syndrome in rats. These findings further suggest that inhibiting the production of nitric oxide in human opioid addicts would be an effective treatment strategy.

Application to Human Drug Therapy

The nitric oxide synthase inhibitors useful in the present method include, as noted above, L-N$^G$-nitroarginine. Also useful in the present method are esters of L-N$^G$-nitroarginine, such as the benzyl and methyl esters, L-N$^G$-monomethylarginine, L-N$^G$-benzylarginine, L-N$^G$-aminoarginine, and L-N-iminoethylornithine. Other NOS inhibitors which can be used in the present invention can be ascertained by routine methods well within the ordinary skill of the art. For example, Dwyer et al. (*Biochem. Biophys. Res. Commun.* 176:1136–41, 1991) provides guidance as to screening methods for determining the NOS-inhibitory properties of various compounds.

The NOS inhibitors useful in the present invention can be used alone, in combination with one another, or in combinations with other classes of drugs useful in attenuating the opioid withdrawal syndrome. The latter include $\alpha_2$-adrenoceptor agonists, of which clonidine is an example; mixed agonist-antagonist opioids, such as buprenorphine; and NMDA antagonists, which block the NMDA-gated ionic channel, such as MK-801 and phencyclidine. When used in combination with these other classes of drugs, the NOS inhibitors of the present invention can serve to attenuate the undesirable side effects of these other drugs, described supra.

In the above-noted applications, the NOS inhibitors of the present invention can be used in the form of their pharmaceutically acceptable salts. These include acid addition salts formed with organic and inorganic acids, such as, for example, hydrochlorides, hydrobromides, sulfates, lactates, phosphates, citrates, fumarates, maleates, acetates, sulfamidates, lactates, tartrates, succinates, methanesulfonates, ethanesulfonates, benzenesulfonates, p-toluenesulfonates, etc.

While the nitric oxide synthase inhibitors of the present invention can be administered by intraperitoneal injection or by continuous infusion, another method of administration is by intravenous drip. Nitroarginine, for example, must be dissolved in acidified saline (pH 1.8). Administration by intravenous drip is suggested because this is the recommended method for administration of other relatively insoluble drugs, e.g., acyclovir, in which the pH of the administered drug would be too acidic or too basic to administer by intramuscular injection. Other pharmaceutically acceptable carriers and injection agents useful in the present invention, depending upon the specific NOS inhibitor(s) and other drugs employed, include, for example, distilled water, saline, etc., and further safe dissolving aids, buffering agents, stabilizers, etc., may be included as well.

Suggested doses of NOS inhibitors for the attenuation of symptoms of the opioid withdrawal syndrome in humans fall within the range of from about 1 µg/kg/day to about 30 mg/kg/day, more preferably from about 1 mg/kg/day to about 25 mg/kg/day, and most preferably from about 3 mg/kg/day to about 15 mg/kg/day. These doses may be given in a single administration via the methods described above, or in two to three doses per day over a 24 hour time period.

With respect to the time course of administration, the nitric oxide synthase inhibitor, or combinations thereof, can be administered orally, intramuscularly, subcutaneously, transdermally, intravenously, or otherwise for about one hour to about two days. During this period, the subject can be maintained on a dose of an opioid sufficient to inhibit spontaneous withdrawal. After a period of about 1 hour to about two days, opioid administration can be discontinued. In either case, administration of NOS inhibitor(s) would be continued for at least about an additional 2–4 days in order to attenuate symptoms associated with eventual withdrawal. Thus, the effective period for administration of the NOS inhibitor ranges from about one hour to about six days. As nitroarginine irreversibly inhibits NOS (Dwyer et al., *Biochem. Biophys. Res. Commun.* 176:1136–41, 1991), enzyme synthesis is necessary for NOS levels to return to normal after discontinuation of inhibitor treatment. This need for enzyme synthesis would extend the effectiveness of the drug beyond the point at which the drug is discontinued.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method for attenuating the symptoms of opioid withdrawal in a human or animal subject, comprising administering to said subject an effective opioid withdrawal symptom attenuating amount of a nitric oxide synthase inhibitor for a period of time effective to attenuate said symptoms upon opioid withdrawal.

2. The method of claim 1, wherein said inhibitor is at least one selected from the group consisting of L-$N^G$-nitroarginine, an ester of L-$N^G$-nitroarginine, L-$N^G$-monomethylarginine, L-$N^G$-benzylarginine, L-$N^G$-aminoarginine, L-N-iminoethylornithine, and a pharmaceutically acceptable salt thereof.

3. The method of claim 2, wherein said ester is selected from the group consisting of a benzyl ester and a methyl ester.

4. The method of claim 2, wherein said pharmaceutically acceptable salt is selected from the group consisting of a hydrochloride, a hydrobromide, a sulfate, a phosphate, a citrate, a fumarate, a maleate, an acetate, a sulfamidate, a lactate, a tartrate, a succinate, a methanesulfonate, an ethanesulfonate, a benzenesulfonate, and a p-toluenesulfonate.

5. The method of claim 1, wherein said administering is conducted orally, intramuscularly, subcutaneously, transdermally, intraperitoneally, by continuous infusion, or by intravenous drip.

6. The method of claim 1, wherein said nitric oxide synthase inhibitor is administered in a pharmaceutically acceptable carrier.

7. The method of claim 6, wherein said pharmaceutically acceptable carrier is selected from the group consisting of distilled water, saline, and acidified saline.

8. The method of claim 6, wherein said pharmaceutically acceptable carrier further comprises at least one of a safe dissolving aid, a buffering agent, or a stabilizer.

9. The method of claim 1, wherein said effective amount of said nitric oxide synthase inhibitor is in the range of from about 1 µg/kg/day to about 30 mg/kg/day.

10. The method of claim 1, wherein said effective amount of said nitric oxide synthase inhibitor is in the range of from about 1 mg/kg/day to about 25 mg/kg/day.

11. The method of claim 1, wherein said effective amount of said nitric oxide synthase inhibitor is in the range of from about 3 mg/kg/day to about 15 mg/kg/day.

12. The method of claim 1, wherein said effective amount is administered in a single dose, or in two to three smaller doses over the course of a 24 hour period.

13. The method of claim 1, wherein said effective period of time is from about 1 hour to about six days.

14. The method of claim 1, wherein said opioid withdrawal is conducted after about two days.

15. The method of claim 1, wherein said opioid withdrawal is conducted after about 1 hour to about six days.

* * * * *